Figure 1:
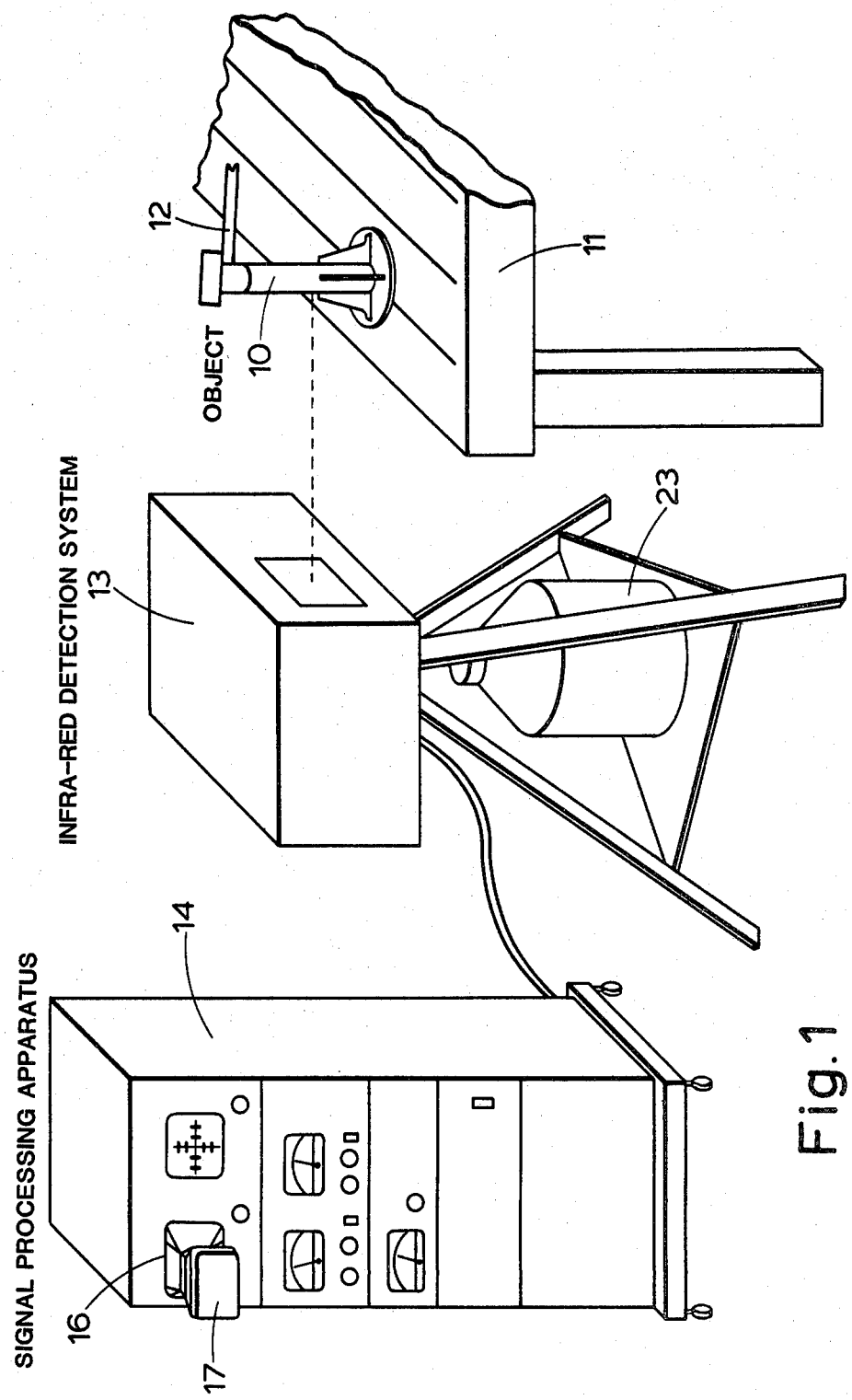

United States Patent [19]

Mountain et al.

[11] 4,378,701
[45] Apr. 5, 1983

[54] APPARATUS AND METHOD FOR INDICATING STRESS IN AN OBJECT

[75] Inventors: David S. Mountain, Portsmouth; Anthony J. Allnutt, Chislehurst; Lionel R. Baker, Orpington; Laurence J. Cox; Alan J. Picot, both of Beckenham; Peter F. Wardropper, West Wickham; Julian M. Webber, Beckenham, all of England

[73] Assignee: Sira Institute Limited, Kent, England

[21] Appl. No.: 179,285

[22] PCT Filed: May 25, 1979

[86] PCT No.: PCT/GB79/00081

§ 371 Date: Jan. 31, 1980

§ 102(e) Date: Jan. 11, 1980

[87] PCT Pub. No.: WO79/01156

PCT Pub. Date: Dec. 27, 1979

[30] Foreign Application Priority Data

May 31, 1978 [GB] United Kingdom .............. 26014/78

[51] Int. Cl.³ .............................................. G01N 3/32
[52] U.S. Cl. ...................................... 73/808; 374/47; 374/121
[58] Field of Search .................. 73/808, 15.6; 356/32, 356/33, 35, 35.5

[56] References Cited

U.S. PATENT DOCUMENTS

1,680,589  8/1928  Bock ..................................... 73/15.6
3,541,851 11/1970  Youmans ............................. 73/15.6
3,934,452  1/1976  Prevorsek et al. ..................... 73/808

*Primary Examiner*—Anthony V. Ciarlante
*Attorney, Agent, or Firm*—Hane, Roberts, Spiecens & Cohen

[57] ABSTRACT

Apparatus and method for indicating stress in an object comprising viewing the temperature variation of part of the surface of the object as it is stressed. An infra-red detector detects small changes of temperature and the stress may be applied by natural loading or by cyclic stressing imposed by a vibrator.

37 Claims, 5 Drawing Figures

APPARATUS AND METHOD FOR INDICATING STRESS IN AN OBJECT

The present invention relates to a method and apparatus for indicating stress in an object.

There are a large number of non-destructive testing techniques at present in use for the analysis of stresses in mechanical structures but many have problems associated with them. Some are difficult to apply and give chiefly qualitative results (eg. brittle lacquers and photo-elasticity), some require prior knowledge of the position and direction of the principal stresses and need careful application (eg bonded strain gauges) and others require complicated apparatus and expert interpretation (eg X-ray or Gamma-ray photography, acoustic emission techniques, laser holography, and moiré fringe methods).

It has been found that heat is produced or absorbed at points of stress in a material undergoing any form of loading or vibration which is believed to be due to the reversible elastic deformation in the material and this produces small, localised temperature changes which may be positive or negative and which are generally proportional to the instantaneous stress magnitude. The present invention incorporates a method and apparatus for utilising this phenomenon.

The present invention provides a method for indicating and distinguishing tension and compression in an object comprising changing the stress in the object and measuring and distinguishing increases and decreases in temperature of a predetermined part of the object with change of applied stress.

In one method the change of stress may be uni-directional and in this case may be caused by a physical shock applied to the object such as a hammer blow.

In an alternative arrangement the stress change may be random and not in a particular direction and under these circumstances the stress change may arise naturally. For example the stress change may arise as random loading of a particular structure such as a bridge.

In a further preferred method, the stress change is cyclic. An impressed or natural cyclic stress change allows conventional signal analysis to be utilised. Thus in a preferred arrangement the cyclic stress change occurs at a predetermined frequency and then by filtering the signal resulting from the measurement of the temperature other effects such as changes in ambient temperature may be eliminated.

The stress change is preferably applied between two spaced points of the object and the predetermined part is arranged to be between these two spaced points. In a preferred arrangement the stress may be produced hydraulically or pneumatically.

In a special case, in which the object is hollow, the stress may be produced by internal hydraulic or pneumatic pressure.

A number of ways may be provided for measuring this temperature change such as contacting techniques using thermocouples or thermistors but we particularly prefer to measure the temperature change by a sensitive detection system which measures the change in thermal radiation emitted by surface areas within the field of view. Such an arrangement may utilise an infra-red detector which preferably may include optical components and which may be movable and of variable focus so that the predetermined part whose temperature is measured is variable.

In a particularly preferred arrangement, the predetermined part of the object whose temperature is measured is scanned across the object.

Before carrying out the method, we may apply a coating to the object having uniform thermal emissivity. The layer may be a thin chemically formed layer and if the object is of metal may be a salt or other compound of that metal.

The present invention also provides a method of determining discontinuities such as cracks, cavities and the like in an object comprising applying a symmetrically cyclic stress to the object and measuring the variation in temperature of a predetermined part of the object and determining any asymmetry in the wave form of the temperature variation.

The invention also provides a method for displaying stress in an object comprising applying a varying stress to the object and presenting a pictorial display of the temperature variation with change of stress across the surface of the object.

The invention also provides a method for indicating stress in an object comprising applying a variable stress between two mechanically constrained spaced points on the object and measuring the variation of temperature of a predetermined part of the object with change of applied stress.

The invention also provides a method of indicating the thickness of a coating on an object comprising applying a cyclically varying stress to the object and measuring the variation in temperature of a predetermined part of the object with change of applied stress, determining the phase difference between the cyclically applied stress and the variation in temperature to indicate the coating thickness.

The present invention provides apparatus for determining discontinuities in an object comprising means for applying a symmetrical cyclic stress to the object and means for measuring the variation in temperature of a predetermined part of the object and signal processing means for determining any asymmetry in the wave form of the temperature variation.

The present invention also provides apparatus for displaying stress in an object comprising means for applying a varying stress to the object and display means for presenting a pictorial display of the variation of temperature with change of stress across the surface of the object.

The present invention also provides apparatus for indicating stress in an object comprising means for applying a variable stress between two mechanically constrained spaced points on the object and means for measuring the variation of temperature of a predetermined part of the object with change of applied stress.

The present invention also provides apparatus for indicating the thickness of a coating on an object comprising means for applying a cyclically variable stress to the object, means for measuring the variation in temperature of a predetermined part of the object with change of applied stress, and signal processing means for determining the phase difference between the cyclically applied stress and the variation in temperature to indicate the coating thickness.

In this case the stress change means may be arranged to vary the stress cyclically at a predetermined frequency such as 50 Hz.

The means for applying the stress may comprise a vibratory hydraulic ram, and in this case the hydraulic means for driving the hydraulic ram may be adapted to provide a control signal in synchronism with the vibration of the ram.

Preferably, there is provided means for mounting the object, and the means for applying the stress is spaced from the means for mounting the object, said apparatus being aligned to indicate the stress in the object at a point between the means for mounting the object and the means for applying the stress.

The means for measuring the variation in temperature may comprise an infra-red detector and there may be provided an infra-red lens for focusing radiation from a point on the object on to the infra-red detector. The lens may be of variable focus. Furthermore there may be provided scanning means whereby the point of the object which is focused on the infra-red detector is scanned across the object. The scanning means may comprise two rotatable mirrors which may be rotated by stepping motors.

Signal processing means may be included for processing the signal produced by the means for measuring the variation in temperature, and the signal processing means may include a bi-directional peak detector for detecting opposite peaks of the output signal of the temperature variation measuring means.

There may be provided display means to receive the output signal from the bi-directional peak detector, the outputs from the stepping motors being utilised to produce a movement of the display signal in a horizontal and vertical direction, and the output signal from the bi-directional peak detector is utilised to vary some characteristic of the display signal. The display means may comprise an oscilloscope and a camera may be focused on the oscilloscope to record the display.

Figure 2:
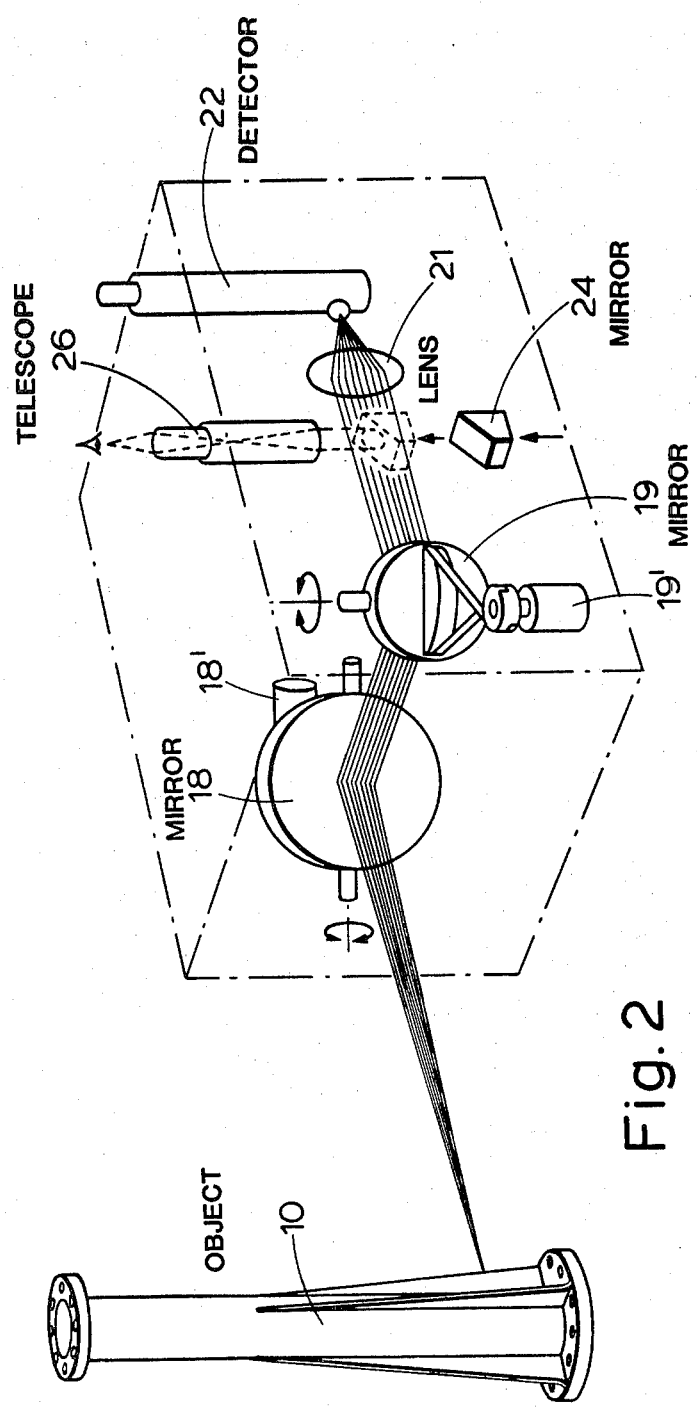
Figure 3:
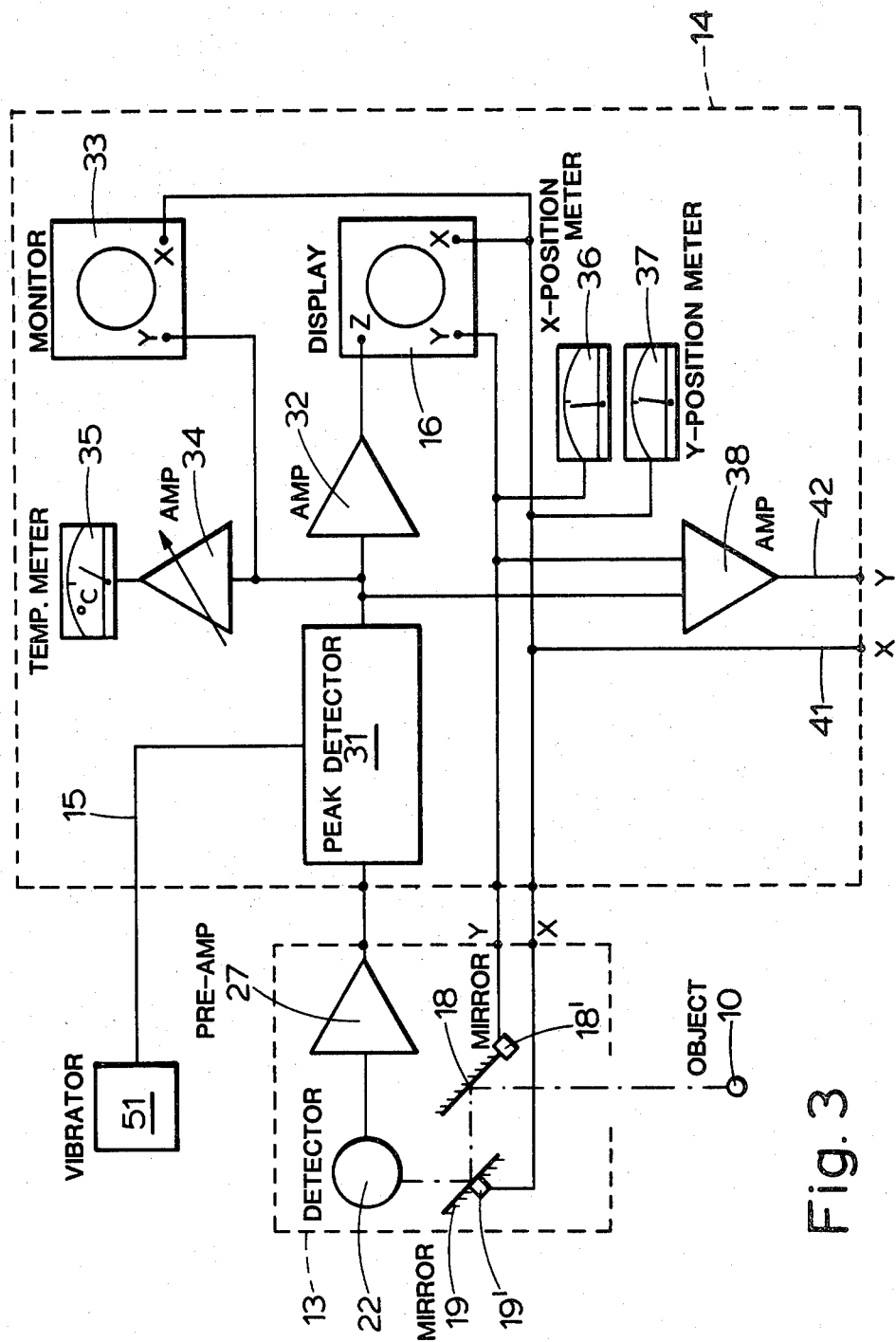
Figure 4:
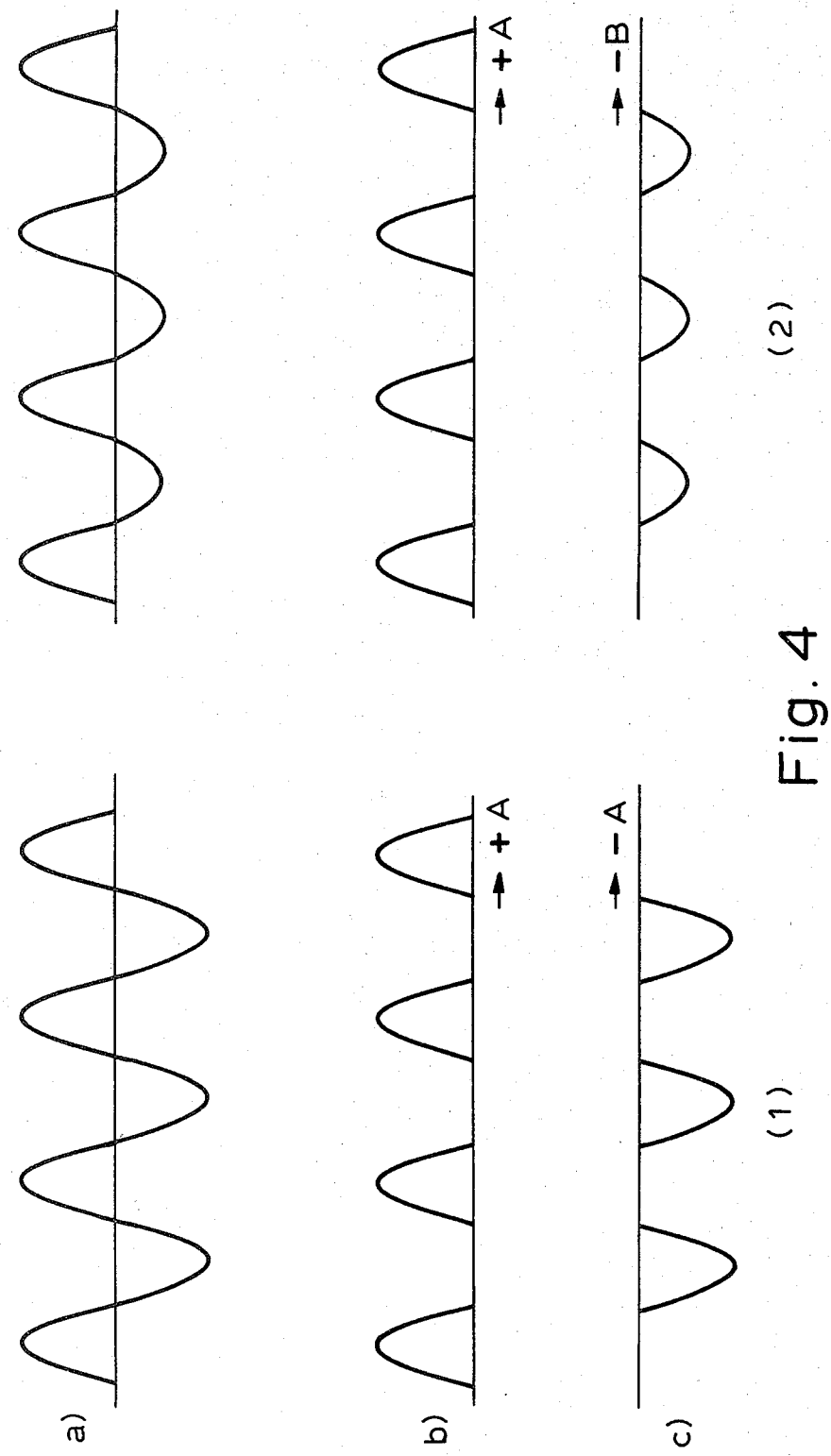
Figure 5:
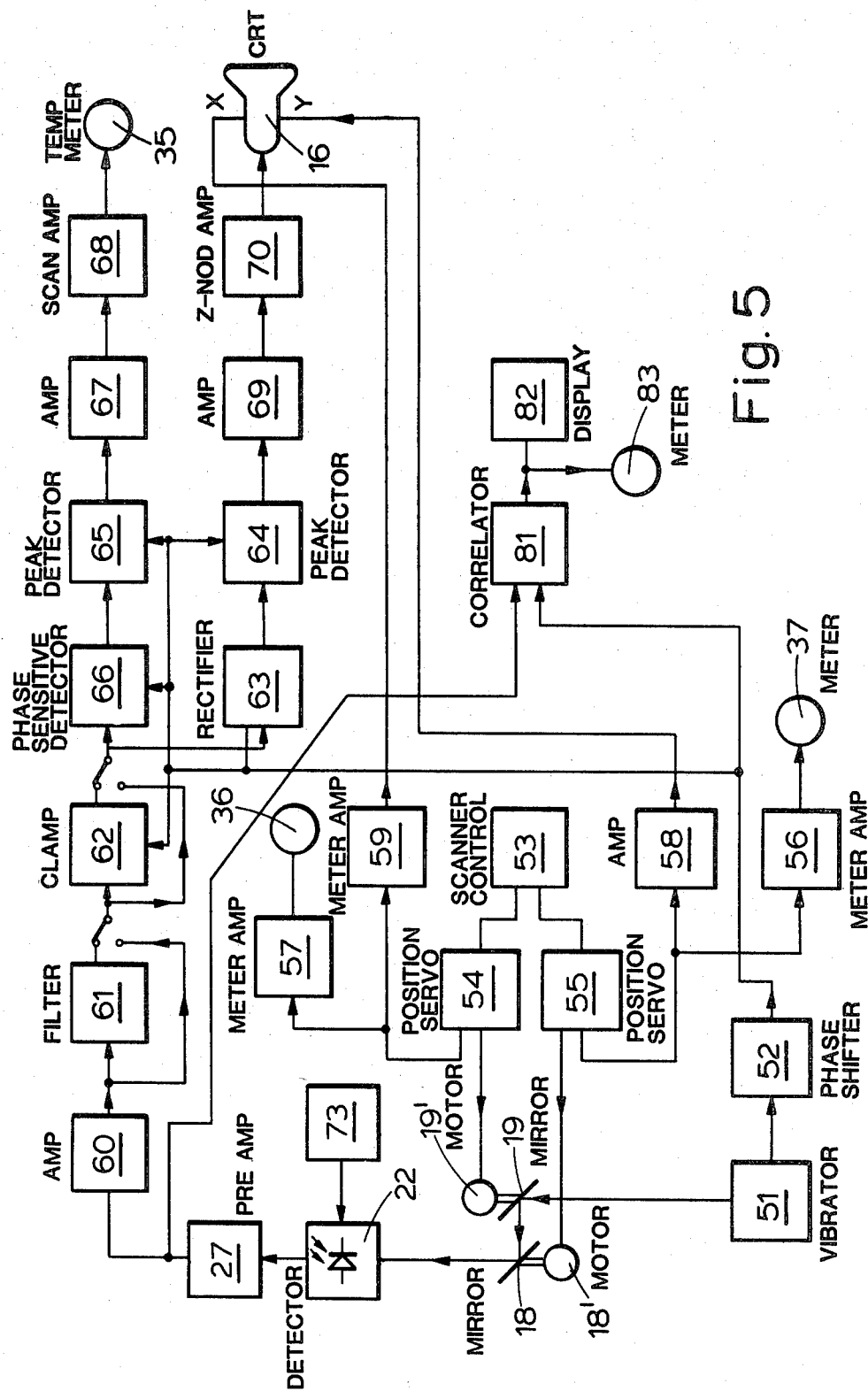

Preferred arrangements of the invention will now be described by way of example only and with reference to the accompanying drawings in which:

FIG. 1 shows a typical layout of apparatus according to the invention in use analysing the stress in an object, FIG. 2 illustrates diagrammatically part of the apparatus shown in FIG. 1, FIG. 3 illustrates in diagrammatic form part of the apparatus including the signal processing apparatus, FIG. 4 illustrates various output signals, and FIG. 5 illustrates in more detail the signal processing apparatus.

The principles of the invention may be applied to various testing environments, for example; the pressure testing of hollow vessels in which a cyclical or shock change of hydraulic or pneumatic pressure is applied within the vessel and the surface temperature change is measured; or in an environment in which an object may be shock tested, for example, by hitting with a hammer or like implement; or the on-site testing of, for example, bridges in which variations in the surface temperature of a stressed part of the bridge will be recorded, the stresses arising during the use of the bridge under wind or traffic loading or for testing the thickness of coatings applied to an object. For ease of understanding, however, a preferred embodiment of the invention will initially be described with reference to the laboratory testing of an object in which stress is applied to the object between two points. This stress may simulate the stress which would arise in practice whereby, if necessary, the limits of stress which may be imposed on the object can be determined and thus proposals made for changes in the design to increase the limits.

The method described here enables the stress pattern on the surface of a structure to be mapped both rapidly and cheaply and identifies the position and spatial distribution of the highest stress points for more detailed analysis for example by strain gauges. It also detects and identifies any discontinuities in the object, particularly cracks, and may be used to determine variations in the thickness of a surface coating. The method also has the advantage of providing direct information on the stress forces being experienced in contrast with the majority of existing techniques which measure deformation (ie. strain), and thus require calibration to the more usually required stress value.

Referring to FIG. 1, the object 10 under test comprises, for example, a base unit for supporting a mast, flagpole, radar aerial or the like. It is mounted to a firm base 11 and is stressed by means of an arm 12 which is driven by a suitable hydraulic or pneumatic ram (not shown in FIG. 1, but illustrated diagrammatically as vibrator 51 in FIGS. 3 and 5). Spaced from the object 10 is an infra-red detection system 13 which will be illustrated in more detail with reference to FIG. 2, the output signal from which is passed to a cabinet 14 incorporating the signal processing apparatus. The cabinet 14 includes a cathode ray oscilloscope 16, to the front of which is attached a camera 17.

The ram is driven so as to oscillate the arm 12 by means of a cyclically variable (vibratory) source of hydraulic pressure (also encompassed by vibrator 51). The variations of stress applied is sinusoidal in this preferred embodiment. A signal representing the pressure waveform is provided by the vibrator 51 on a signal line 15 (FIG. 3) although for some uses we only need a trigger pulse.

Referring to FIG. 2, the infra-red detection system 13 comprises a scanning system in the form of two orthogonal mirrors 18, 19 driven by respective stepping motors 18', 19' which rotate them about horizontal and vertical axes respectively to produce a linear, raster or spiral scan. The optical components (we shall refer to optical as including infra-red) includes an infra-red lens 21 which focuses the radiation on to a detector 22 which may comprise one infra-red detector or a linear or a two dimensional array of infra-red detectors which are maintained at a constant temperature by suitable means such as liquid nitrogen supplied from a flask 23 (FIG. 1), liquid helium or a thermoelectric cooler. In the case of a detector array, signals collected by such an array can be processed in parallel or sequentially. Movable so as to interrupt the beam in front of the lens 21 is a mirror 24 which reflects the beam through a viewing telescope 26.

It will be understood that with this arrangement radiation from a small part or area of the object is focused on to the detector 22 and the area viewed is scanned across the object by means of movement of the mirrors 18, 19 in a conventional manner. Furthermore, the focus of the apparatus is variable by movement of the lens 21 to thereby vary the object plane from which infra-red is to be received. The performance of the lens is optimised by setting of an aperture stop. The control of this stop aperture increases the depth of focus of the system and allows accurate stress measurements to be made over non flat surfaces. The lens is of variable focal length so that the field of view can be varied. A wide field is required for rapid examination of a large area of the object, more detailed measurements across small areas of the object being accomplished by increasing the focal length.

There may be provided optical means to compensate for movement of the part of the object being examined under the effect of cyclic stress.

The direction of pointing of the instrument is chosen to select a particular stress profile across the surface of a structure to be recorded. By varying the motions of the optical scanning system the desired display resolution of the selected stress area is obtained.

In place of the mirrors alternative image scanning systems could include the use of Nipkow discs, x-y, or angular movements of detector or lens, and polygon raster mirrors (mirror drums).

Referring to FIG. 3, therefore, by scanning the point which is being examined across the object an output signal is produced by the detector 22 which is amplified in a pre-amplifier 27 within the infra-red detection system 13 and the output signal from the pre-amplifier is passed to a signal processing apparatus within cabinet 14.

The electronic pre-amplifier 27, operating close to the detector 22, is designed to have low noise over the range of measuring frequencies. For thermal measurement by means of cooled infra-red detectors an electronic bias system permits the detector to be operated at zero bias where the noise generated by the detector is a minimum.

Outputs from the motors 18', 19' driving the mirrors 18, 19 are also passed to the signal processing apparatus so as to give information as the position of the area which is being examined at any one time.

The signal processing apparatus comprises a bi-directional peak detector 31, a non linear amplifier 32, a visual display unit 16 in the form of an oscilloscope 33, a monitoring oscilloscope 33, a variable amplifier 34, a peak temperature meter 35 an x position meter 36 and a y position meter 37 with a further amplifier 38.

The trigger pulse from the vibrator 51 is also fed by line 15 to the bi-directional peak detector 31.

The apparatus described so far operates as follows. The infra-red detection system 13 is aligned with the object 10 and the optics are arranged so as to focus an area of the object 10 on to the detector 21. This may be checked by inserting the mirror 24 into the beam path in front of the lens 21 whereby the viewing telescope may be utilised to view the exact point under consideration.

The apparatus is then switched on so that the arm 12 vibrates cyclically to stress the object 10 cyclically between the two mechanically constrained spaced points viz: the point of contact with the arm 12 and the base of the object 10. In the present example the point which is being viewed by the infra-red detection system is between these two points.

As the object is stressed then the temperature of its surface varies depending upon the stress of the material underlying that surface and clearly this will vary cyclically with the cyclical variation of stress by the arm 12. As an example only the arm 12 vibrates at a predetermined frequency of between 0 and approximately 70 Hz, typically 30 Hz and may be adjustable.

As mentioned above, rotation of the mirrors 18 and 19 back and forth scans the point being viewed across the object and output signals from the motors rotating the mirrors 18 and 19 are passed to the signal processing unit. Furthermore, the output of the detector 22 is also passed to the signal processing unit. The output from the detector 22 is passed to the bi-directional peak detector 31 which also receives the trigger pulse from the vibratory apparatus. The peak detector 31 passes a peak signal to the non-linear amplifier 32 and thence to the Z input of the CRO 16. The output signal of the detector 31 is also passed through the amplifier 34, to the peak temperature meter 35 to the amplifier 38 and to the y plates of the monitoring oscilloscope 33.

The output signal from the motor 19' driving the mirror 19 (which rotates about a vertical axis) and will be referred to as the x mirror is passed to the x plates of the CRO 16, to the x meter 37, to the x plate of the oscilloscope 33, and to an x output 41 from the signal processing equipment. The signal from the motor 18' driving the mirror 18 (the y mirror) is passed to the y meter 36, to a further input of the amplifier 38 and to the y plate of the CRO 16. The output from the amplifier 38 is passed to a y output line 42.

Thus the CRO 16, by virtue of the signals to the x and y inputs, scans the cathode ray across the oscilloscope in synchronism with the scanning of the viewed area across the object 10 by the mirrors 18, 19. The brightness of the cathode ray beam is controlled in accordance with the signal from the bi-directional peak detector and therefore is generally in proportion to the temperature change of the point under examination. This is arranged so that a point which is of higher temperature change than another point will be indicated more brightly.

It will be understood, therefore, that as the CRO 16 is viewed by the camera 17, a two dimensional picture of the object is built up in which the areas of greater stress are more brightly illuminated than other areas. In this way a picture is built up and recorded in the camera which gives a very clear indication of the stress distribution across the object.

The monitoring oscilloscope 33 provides a profile stress plot for a scan along one section of the object. (ie in one dimension).

The signals on line 41, 42 may be recorded for example on magnetic tape for subsequent analysis.

The detector is particularly sensitive and in practice can measure down to and distinguish increases and decreases of temperature of 0.001° C.

It will be understood that the ambient temperature of the object may well vary by considerably greater than 0.001° C. in a relatively short time. The present apparatus, by cycling the stress at, for example, 30 Hz allows this variation of temperature to be eliminated by the bi-directional peak detector which only picks up the maximum and minimum temperatures during the course of several complete cycles of stress.

A further point to note is that as trigger pulses are provided from the vibrator 51 which are at a known phase point with respect to the stress waveform, their relative phase to the signals detected by the bi-directional peak detector 31 can be established. It will be understood that comparison of the phase of the signal from the pre-amplifier 27 with the trigger pulse from the vibrator 51 allows one to determine whether or not a particular part of the object is under compression or tension with respect to a particular applied force. Thus if the output of the detector and hence the preamplifier 27 indicates an increase in temperature of the point under examination whilst the pulse or pressure waveform from the vibratory apparatus indicates that a positive force is being applied to the object, we can deduce that, for that point, a positive force causes a compression.

In the simpler case of a unidirectional application of stress without cycling then simply determining whether the point under test increases or decreases in temperature will ascertain whether it is under compression or tension.

It has been found that where at points or areas of a structure or object there is a structural fault or material defect, for example, a crack or void, the localised stress changes which result from applied loading or vibration may differ from stress changes that occur in the absence of any defect. The temperature changes which will result from the instantaneous local stress changes at these points may then be different from temperature changes detected from a non-faulted structure. The location may be found by means of measurement of the infra-red radiation emitted when the structure or object is undergoing loading forces.

Means for the processing of the output signal of the infra-red detector to produce this result will be described with reference to FIG. 5.

FIG. 5 illustrates diagrammatically and in more detail the apparatus of FIG. 3 with some additions. The vibrator 51, phase shift apparatus 52, scanner control unit 53, position servos 54, 55, horizontal meter amplifier 56, vertical meter amplifier 57, x amplifier 58, y amplifier 59, variable gain variable bandwidth amplifier 60, 1.5 Hz high pass filter 61, black level clamp 62, precision rectifier 63, positive peak detector 64, and positive and negative peak detector 65 together form the bi-directional peak detector 31 of FIG. 3, phase sensitive detector 66, variable threshold amplifier 67 and amplitude scan amplifier 68 together form the variable gain amplifier 34 of FIG. 3 variable threshold amplifier 69, and and Z-mod amplifier 70 together form the non-linear amplifier 32, of FIG. 3, and in addition to the parts shown in FIG. 3 there is provided a zero bias control (auto or manual) 73, a substractor or harmonic analyser or correlator 81, a fault display 82 and fault meter 83.

The apparatus shown in FIG. 5 operates in a generally similar manner to that shown in FIG. 3.

The parts 81, 82, 83 provide a fault detection system for carrying out a method to be described with respect to FIG. 4.

FIG. 4 (1a) shows the waveform of the pressure applied to the hydraulic ram and hence the waveform of the stress applied. It is sinusoidal. As the temperature variation at any point follows the variation in stress, FIG. 4 (1a) is also a plot of the waveform of the temperature variation (ie the infra-red emission output) at any one normal point.

In FIGS. 4 (1b) and 4 (1c) the portions of the waveform above and below the temperature value at zero stress (in this case the mean value) have been separated.

FIG. 4 (2a) shows a typical infra-red emission output waveform at a fault point of an object (eg a crack or void). The shape of the waveform at the fault point is dependent upon the characteristic of the fault, loading forces applied, frequency of loading, and material properties, but as can be seen is unsymmetrical. This can be simply explained in the extreme case of a crack. When the area about the crack is compressed then that compression is transmitted by the crack. When, however, the area is under tension then the crack does not transmit the tension and hence an output waveform is produced corresponding to FIG. 4 (1b). In the case of other discontinuities in the object some tension is transmitted but not as efficiently as the compression and hence a waveform 4 (2a) is produced. (There are circumstances in which the opposite is true, ie tension is transmitted but not compression eg a cavity in the resin in a glass fibre.) By detection of the infra-red radiation by means of the described equipment typical points of fault can be determined and displayed on the oscilloscope 16.

By means of the measurement of the phase of the waveform the positive and negative components of the output waveform with respect to the zero stress level is determined (ie FIGS. 4 (2a) and 4 (2b) respectively. By subtraction of these two signals, for example, an indication of the characteristics and severity of the fault is provided. Thus if there is no fault of this type present this subtraction produces a nil result. If there is a fault present the subtraction produces a finite result.

Alternatively the asymmetry of the waveform can be determined by Fourier analysis. As will be understood if the waveform is a symmetrical sine wave then Fourier analysis produces a single frequency component whereas if there is any asymmetry then more than one frequency component is detected.

Thirdly, the asymmetry of the waveform can be detected by the correlation of the waveform with the harmonics of the applied stress waveform whereby a symmetrical waveform gives a nil output but an asymmetrical waveform gives a finite output. The output from the electronic processing system for fault detection eg subtraction or Fourier analysis or correlation systems is provided as a meter display (83) when viewing a single point. Alternatively the position shape and characteristics of the fault can be displayed as an area of intensity on the oscilloscope 16 when a surface area of the structure is under examination.

With regard to the display system, a visual channel (now shown in FIG. 5) can provide the operator with magnification to identify features on the test structure which are related to the stress outputs, the two channels, infra-red and visible being made optically coincident. Alternative means of providing a visual display other than the oscilloscope 16 include TV detector, projection screen etc. The signals generated by the infra-red detector could be used to modulate photo-emitting diodes in the field of view of an operator and so give an indication of the direction an extent of the scan and magnitude of the stress for instantaneous observation or photographic recording. A laser projection system could also be used to pinpoint the particular area under measurement.

The signal outputs are used to display a contour map of stress, by means of lines at equal stress levels or coloured regions between chosen levels on the TV display monitor or by numerals indicating stress levels superimposed on a picture of the object.

A threshold control (16) is provided to highlight areas of high stress and to increase display sensitivity between chosen stress levels.

For the method and apparatus to operate accurately, it has been found best to have the object coated with a coating having uniform thermal emissivity. This is preferably in the form of a thin chemically formed layer and in the case where the object is a metal, the coating may be a salt or other compound of the metal concerned. In a preferred arrangement, in which the object is of aluminium, the coating may be produced by anodisation.

Calibration facilities can be included with the measuring system. For example, in order to correlate output signals with surface temperature a controlled thermal source can be used.

In order directly to calibrate output with stress levels, standard test structures can be used with, for example, strain gauges.

Calibration for structures of varying surface emissivity can be made by using standard test pieces.

Means can be included in the equipment for measuring stress distribution for the automatic measurement and compensation for emissivity values and variations on the surface to be examined. The compensation can be made either simultaneously with infra-red radiation measurements, by for example measurement of surface emissivity using a controlled infra-red source, or by preliminary measurements whereby the observed structure is examined when no loading is being applied.

The peak detector 31 can be reset by the triggering signal produced by transducers in the object vibrator 51. An important feature of the instrument is the means provided for the adjustment in phase between the waveform of the applied stress and the waveform of the temperature signals to compensate for thermal lag of coatings and errors in transducers.

According to a further aspect of the invention the thermal lag of coatings on the object can be investigated using their affect on the phase difference between the waveform of the applied stress and the waveform of the temperature signals. In FIG. 5 the temperature variation is detected as described before with reference to FIGS. 3 and 5 by means of the components 18, 19, 22 and 27 and the output from the pre-amplifier 27 is passed to the phase sensitive detector 66 via components 60, 61 and 62. Furthermore, the output waveform of the applied stress is applied from the vibrator 51 via phase shift apparatus 52 to the phase sensitive detector 66. The phase sensitive detector 66 produces a signal output depending on the difference between the phase of the waveform of the applied stress (from vibrator 51) and the waveform of the temperature signal (from amplifier 27). This output signal is fed to the oscilloscope 16 so as to produce a pictorial representative of the object. In this case, however, instead of the pictorial representative of the object representing, by means of variation of brightness, the variation in stress across the object, it illustrates the variation in the phase lag between the two signals across the object and hence the thickness of the coating across the object. By simple switching one may then display on the oscilloscope 16 either a pictorial representation of the stress across the object or a pictorial representation of the thickness of the coating on the object.

Such an arrangement and method may be utilised with various shapes of objects and may be utilised, for example, with plane sheet material but has particular use in the examination of the thickness of coatings on complex shaped objects which are at present difficult to monitor. As before the thickness of the coating across the object is displayed pictorially either in the forms of variation of brightness of the spot on a cathode ray oscilloscope or by means of variation of colour, or contour lines joining points of equal thickness of coating, or by numerals representing the thickness of the coating.

The method may be further improved by varying the frequency of the applied stress.

The method and apparatus described provide a technique of obtaining by non contact means information on the stress characteristics of a system simultaneously with system loading. This method and apparatus can be applied not only to model structures in order to assess design characteristics but can also be used on real structures. The apparatus can be used not only to measure stress distribution in a system but also the thickness of surface coating and may detect and determine the magnitude and characteristics of defects in materials and structures. The material defects detected include fatigue cracks, faulty welds, internal cavities etc. Signal outputs obtained with the technique are used to assess the elastic properties of a material in a structure undergoing loading.

In contrast with most stress analysis systems the technique allows a simple measurement of the stress properties of a structure undergoing a wide range of dynamic loading and hence gives information on the vibration characteristics of the system.

We claim:

1. A method for indicating and distinguishing tension and compression in a predetermined part of a complex shaped object comprising determining a continuously changing load on the object and measuring and distinguishing increases and decreases in temperature of the predetermined part of the object with change of load, said measuring of the temperature being performed by determining the thermal radiation of the predetermined part and correlating these changes of temperature with respect to the instantaneous value of the continuously changing load.

2. A method as claimed in claim 1 in which the load change is unidirectional.

3. A method as claimed in claim 1 in which the load change is random.

4. A method as claimed in claim 1 in which the load change is applied and is cyclic.

5. A method as claimed in claim 4 in which the load change changes cyclically at a predetermined frequency.

6. A method as claimed in claim 4 or 5 in which the relative phase of changes of temperature of the predetermined part of the object and the change of applied load is determined whereby to determine whether a particular applied load produces tension or compression in that predetermined part of the object.

7. A method as claimed in claim 6 in which the load change is applied between two mechanically constrained spaced points of the object and said predetermined part is between said two spaced points.

8. A method as claimed in claim 1 in which the temperature of said predetermined part is measured by an infra-red detector.

9. A method as claimed in claim 1 in which the predetermined part of the object whose temperature is measured is scanned by thermal radiation determining means.

10. A method as claimed in claim 1 in which before testing the object, a coating is applied having uniform thermal emissivity.

11. The method as claimed in claim 1 further including a method of determining discontinuities in the object in which a cyclic load is applied by comparing in an analyser a waveform received from a load applying means with a temperature variation waveform received from a temperature detecting means to determine any assymmetry in the latter waveform.

12. Apparatus for indicating and distinguishing tension and compression in a predetermined part of a complex shaped object comprising means for determining a continuously changing load on the object, thermal radiation determining means for measuring and distinguishing increases and decreases in temperature of the predetermined part of the object with change of the load applied to the object and signal processing means for receiving a signal from said measuring and distinguishing means and from said load determining means to correlate these signals to produce an output indicating and distinguishing tension and compression at said part.

13. Apparatus as claimed in claim 12 in which the apparatus further includes means for recording the signal produced by the temperature measuring means, whereby the recorded signal may thereafter be passed to the signal processing apparatus.

14. Apparatus as claimed in claim 13 in which a means for applying load to the object is arranged to vary the load cyclically at a predetermined frequency.

15. Apparatus as claimed in claim 14 in which the means for producing the load comprises a vibratory hydraulic ram.

16. Apparatus as claimed in claim 15 in which the hydraulic means for driving the hydraulic ram is adapted to provide a control signal in synchronism with the vibration of the ram.

17. Apparatus as claimed in claim 12 in which a means for applying load to the object is arranged to vary the load cyclically at a predetermined frequency.

18. Apparatus as claimed in claim 12 in which the means for measuring the variation in temperature comprises an infrared detector.

19. Apparatus as claimed in claim 18 in which there is provided an infrared lens for focusing radiation from the part of the object on to the infra red detector.

20. Apparatus as claimed in claim 12 further including means for applying a varying load to the object and display means for presenting a pictorial display of the variation of temperature with change of load across the surface of the object.

21. Apparatus as claimed in claim 20 in which the display means is adapted to provide a two dimensional display.

22. Apparatus as claimed in claim 20 in which the display means is adapted to display temperature variation by means of variation of brightness.

23. Apparatus as claimed in claim 20 in which the display means is adapted to display temperature variation by means of variation of colour.

24. Apparatus as claimed in claim 20 in which the display means is adapted to display temperature variation by means of contour lines.

25. Apparatus as claimed in claim 20 in which the display means is adapted to display temperature variation by means of variation of numerals.

26. Apparatus as claimed in claim 20 in which there is provided scanning means for scanning the part of the object whose temperature variation is measured.

27. Apparatus as claimed in claim 26 in which the apparatus is adapted to provide a linear scan.

28. Apparatus as claimed in claim 26 in which the apparatus is adapted to provide a raster scan.

29. Apparatus as claimed in claim 26 in which the apparatus is adapted to provide a spiral scan.

30. Apparatus as claimed in claim 26 in which the scanning means comprises two rotatable mirrors.

31. Apparatus as claimed in claim 30 in which stepping motors are provided to rotate the mirrors.

32. Apparatus as claimed in claim 31 in which the signal processing means includes a bidirectional peak detector, the outputs from the stepping motors being utilized to produce a movement of the display signal in a horizontal and vertical direction and the output signal from the bidirectional peak detector being utilised to vary some characteristic of the display signal.

33. Apparatus as claimed in claim 32 in which the display means comprises an oscilloscope.

34. Apparatus as claimed in claim 33 in which a camera is focused on the oscilloscope to record the display produced.

35. Apparatus as claimed in claim 12 including means for applying a variable load between two mechanically constrained spaced points on the object.

36. Apparatus as claimed in claim 35 in which there is provided means for mounting the object, and the means for applying the load is spaced from the means for mounting the object, said apparatus being aligned to indicate the load in the object at a point between the means for mounting the object and the means for applying the load.

37. Apparatus as claimed in claim 12 further including means for applying a cyclic load to the object and means connected to receive signals from the load applying means and from the measuring means for determining any difference between the waveform of the cyclic load and the wave form of the temperature variation whereby to determine discontinuities in the object.

* * * * *